US011751809B2

(12) United States Patent
Joutsen et al.

(10) Patent No.: US 11,751,809 B2
(45) Date of Patent: Sep. 12, 2023

(54) BRA FOR MEASURING A PHYSIOLOGICAL SIGNAL

(71) Applicant: Clothing Plus MBU Oy, Kankaanpaa (FI)

(72) Inventors: Atte Joutsen, Tampere (FI); Kirsi Vanhatalo, Honkakoski (FI)

(73) Assignee: Clothing Plus MBU Oy, Kankaanpaa (FI)

( * ) Notice: Subject to any disclaimer, the term of this patent is extended or adjusted under 35 U.S.C. 154(b) by 475 days.

(21) Appl. No.: 16/611,675

(22) PCT Filed: May 9, 2018

(86) PCT No.: PCT/FI2018/050353
§ 371 (c)(1),
(2) Date: Nov. 7, 2019

(87) PCT Pub. No.: WO2018/206853
PCT Pub. Date: Nov. 15, 2018

(65) Prior Publication Data
US 2020/0146627 A1 May 14, 2020

(30) Foreign Application Priority Data
May 9, 2017 (FI) .................................... 20175416

(51) Int. Cl.
*A61B 5/00* (2006.01)
*A61B 5/25* (2021.01)
(Continued)

(52) U.S. Cl.
CPC ............ *A61B 5/6804* (2013.01); *A41C 3/005* (2013.01); *A41C 5/00* (2013.01); *A61B 5/0531* (2013.01);
(Continued)

(58) Field of Classification Search
CPC ..... A61B 5/6804; A61B 5/282; A61B 5/0531; A61B 5/6823; A61B 2562/12; A41C 3/005; A41C 5/00
See application file for complete search history.

(56) References Cited

U.S. PATENT DOCUMENTS

2008/0153388 A1   6/2008  Liu
2008/0287769 A1*  11/2008 Kurzweil ............. A61B 5/0535
                                                      600/509
(Continued)

FOREIGN PATENT DOCUMENTS

CN     104397888 A    3/2015
CN     105266765 A    1/2016
(Continued)

OTHER PUBLICATIONS

Carroll Erin A et al: "Food and Mood: Just-in-Time Support for Emotional Eating", 2013 Humaine Association Conference on Affective Computing and Intelligent Interaction, IEEE, Sep. 2, 2013 (Sep. 2, 2013), pp. 252-257, XP032530289, ISSN: 2156-8103, DOI: 10.1109/ACII.2013.48.
(Continued)

*Primary Examiner* — Adam Z Minchella
(74) *Attorney, Agent, or Firm* — Young Basile Hanlon & MacFarlane, P.C.

(57) ABSTRACT

A bra for measuring a physiological signal from a body of a user wearing the bra comprises first and second front portions, or bra cups portions. The bra also comprises first and second side wings, wherein the first side wing is coupled with the first front portion and the second side wing is coupled with the second front portion. In addition the bra comprises a measuring device and/or at least two electrodes, where the measuring device or at least one electrode is arranged to a module, and the module forms at least a basis
(Continued)

of the first side wing of the bra or even the first side wing of the bra as its entirety.

18 Claims, 2 Drawing Sheets

(51) Int. Cl.
    *A41C 3/00*     (2006.01)
    *A41C 5/00*     (2006.01)
    *A61B 5/0531*     (2021.01)
    *A61B 5/282*     (2021.01)

(52) U.S. Cl.
    CPC ............ *A61B 5/282* (2021.01); *A61B 5/6823* (2013.01); *A61B 2562/12* (2013.01)

(56) References Cited

U.S. PATENT DOCUMENTS

| | | | |
|---|---|---|---|
| 2013/0281815 A1 | 10/2013 | Varadan | |
| 2015/0335078 A1 | 11/2015 | Zhang | |
| 2017/0311886 A1* | 11/2017 | Chausiaux | A61B 5/6802 |
| 2018/0249767 A1* | 9/2018 | Begriche | A41D 1/005 |

FOREIGN PATENT DOCUMENTS

| | | |
|---|---|---|
| CN | 205019029 U | 2/2016 |
| CN | 205214223 U | 5/2016 |
| CN | 205459740 U | 8/2016 |
| CN | 205672018 U | 11/2016 |
| CN | 106343623 A | 1/2017 |
| DE | 202015106685 U1 | 2/2016 |
| ES | 2238193 A1 | 8/2005 |
| FI | 20155698 A | 4/2017 |
| WO | 2016063082 A1 | 4/2016 |

OTHER PUBLICATIONS

Kim, J. et al. "Highly wearable galvanic skin response sensor using flexible and conductive polymer foam." In: Annual International Conference of the IEEE Engineering in Medicine and Biology, 2014, pp. 6631-6634.

Office Action with English Translation issued by the China Patent Office in the corresponding application No. 201880045311.6 dated Jan. 28, 2022.

* cited by examiner

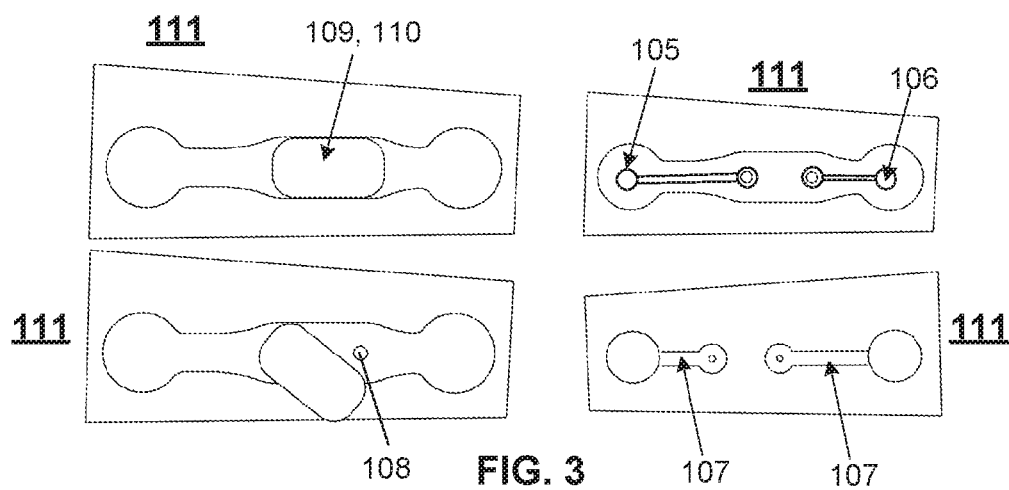
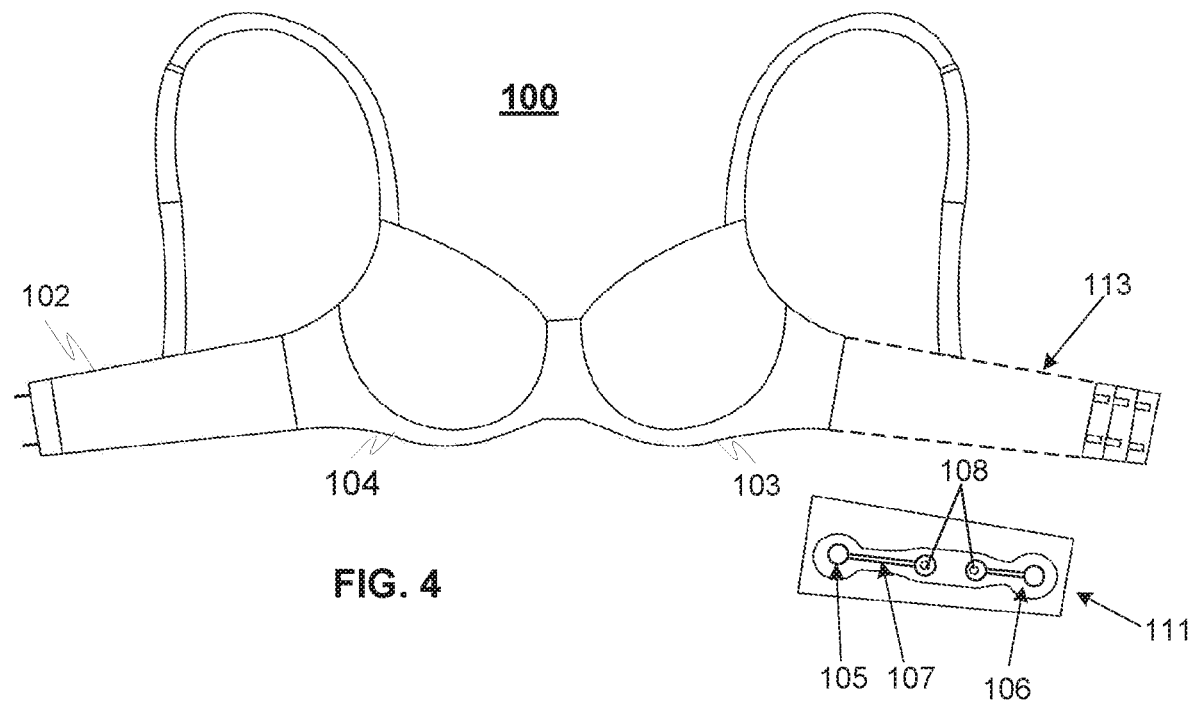
FIG. 3
FIG. 4

BRA FOR MEASURING A PHYSIOLOGICAL SIGNAL

CROSS REFERENCE TO RELATED APPLICATION

The present application claims priority to Finnish Patent Application No. 20175416, filed May 9, 2017, incorporated herein in its entirety.

TECHNICAL FIELD

The invention relates to a bra for measuring a physiological signal, advantageously an electrical signal from a body of a user wearing the bra. In addition, the invention relates to a method for manufacturing the bra.

BACKGROUND

A measuring of physiological signals, such as ECG for heart rate detection, is commonly known by using e.g. dry (i.e. water moistened) electrodes integrated into sports bra. In the sports bra the mids of the electrodes are typically located about 10 cm from the body midline on the left and right side of the body just under the bra cups. In addition, the physiological signals can also be measured using e.g. the dry electrodes integrated into womens daily worn bra.

There are however some disadvantages relating to the known prior art, such as that majority of the current daily worn bra or leisure bra models have little or no fabric under the cups that could incorporate the measurement electrodes to similar positions as in the sports bra. In the sports bra there is often an elastic underband which has space for sensors and measuring electronics. However, this approach cannot be used in the daily worn bra, because daily worn bra should typically be skin-tight and comfortable for worn whole day so in other words there is no space for additional sensor package or the like under the cups.

Furthermore additional disadvantages are also related to the known prior art, where the electric components are integrated into or onto the structure of the garment, such as the bra, at a manufacturing stage of the garment. Very often the garment manufacturer needs to manufacture and install one electric component to a certain location, another electric component to another location and provide suitable power and signal lines between the components. Thus the garment manufacturer needs to have also knowledge also about the field of electronics. Other possibility is that the manufacturer sends a semi-finished garment, such as the bra, to an electronic component manufacturer, who manufactures the components and installs them into or onto the semi-finished garment and again sends the semi-finished garment with the installed electronic components to the garment manufacturer for the finishing stage.

In addition designing of the electronic components raises often numbers of special issues which are not always very clear for the manufacturers of the garments, such as the bra manufacturer. Furthermore there is a disadvantage relating to recycling of the garments after their lifetime, because they includes electronic components with materials, like metals and especially heavy metals used in electronic components and batteries, which should be recycled separately from the garment material, like textile or fabric. For example the components integrated into the structure of the bra might be very difficult to find and remove.

SUMMARY

An object of the invention is to alleviate and eliminate the problems relating to the known prior art. Especially the object of the invention is to provide a bra for measuring a physiological signal from a body of a user wearing the bra so that electronics, especially electrodes and conductive leads as well as also connectors can be integrated to the bra structure easily and so that also the manufacturer without any knowledge about the measuring technology can manufacture the bra so that the measuring of the physiological signals is possible and in addition so that there is no need for example to send the semi-finished product to the expert of the measuring technology field.

The object of the invention can be achieved by the features of independent claims.

The invention relates to a bra for measuring a physiological signal from a body of a user wearing the bra according to claim 1. In addition the invention relates to a manufacturing method of the bra according to claim According to an embodiment of the invention a bra for measuring a physiological signal comprises first (left) and second (right) front portions, such as bra cups (or at least imaginary portions), and first (left) and second (right) side wings. The first end of the left side wing is advantageously coupled with the first front portion and the first end of the second side wing with the second front portion. The second ends of the side wings are extended so that they can be connected to each other in the back side of the used during the use.

According to an embodiment the bra additionally comprises a measuring device for measuring the physiological signal from a body of a user wearing the bra. The measuring device may comprise e.g. at least two electrodes, where at least one electrode is arranged to the first side wing of the bra.

Advantageously also another electrode is arranged to the first side wing.

The measuring device may also comprise an optical, temperature, or strain gauge integrated to the first side wing. The physiological signal to be measured is e.g. ECG signal for heart rate detection, but can also be bioimpedance, or EDA (electro dermal activity) (also known as GSR (Galvanic Skin Response)) signal, for example.

According to an embodiment, the measuring device or at least one electrode is arranged to a module, where the module forms at least a basis of the first side wing of the bra. The basis means according to an embodiment at least a major portion of the side wing structure, whereupon for example only a trim or stitching ribbon or other minor portion can still be added for example to support and fasten the module to the structure of the bra. Advantageously the major portion is at least 60%, more advantageously at least 70% and most advantageously more than 80% of the whole side wing structure. In particularly the module is configured to form at least a bearing structure or portion of the first side wing of the bra. According to another embodiment the module may form the first side wing of the bra as its entirety.

As an example the electrodes are as positive and negative electrodes, and they are advantageously suitable for measuring electric signal from the body of said used as the physiological signal. According to an embodiment the first electrode is a positive electrode and the second electrode is a negative electrode and they are arranged to the first side wing so that said first electrode is arranged between the second electrode and the first front portion of the bra. In other words the positive electrode is arranged into the left side wing next and close fabric just left to the left side cup and negative electrode is integrated into the fabric that extends over the left side of the body towards the back.

The bra advantageously comprises also conductive lead material integrated to the first side wing material. The lead material may be e.g. conductive fabric, which is laminated to the first side wing. Advantageously the conductive lead fabric does not bind the bra fabric and thereby allows both materials to stretch and thus user comfort is retained. The bra advantageously comprises also connectors and leads, where the leads couple the electrodes and connectors electrically together. According to the invention the connectors and leads are both arranged to the first side wing. In addition the bra comprises also a data measuring and/or processing unit, transmitter and/or power source, which are also advantageously arranged to the first side wing.

It is to be noted that the connectors, leads, measuring, processing unit, transmitter and/or power source can be arranged to a module. Also at least one electrode can be arranged to the module. Advantageously the module is then integrated to the bra as the first side wing or as a portion of the first side wing. The module can be e.g. sewn or laminated to the first side wing, but also other fixing method can be applied.

The electrode used can naturally be any suitable electrode, but according to an advantageous embodiment the electrode used is a dry electrode. The using of the dry electrode offers advantages namely there is no need to use any conductive gel or even moisturising the sensor area for enabling good electrical contact between the skin and the electrode. Furthermore the dry electrode garment can be washed. In addition it is to be noted that the invention is very suitable also for a daily worn bra, where there is very limited space for measuring devices and electrodes under the cups area that could incorporate the measurement electrodes to similar positions as in the sports bra.

The present invention offers advantages over the known prior art, such as allowing elastic and comfort measuring platform also for daily worn bra models, which typically have little or no fabric under the cups that could incorporate the measurement electrodes to similar positions as in the sports bra. In addition the manufacturing is easy and fast and reliable process even if the garment manufacturer have no or minimal knowledge about the field of electronics. Neither there is need for sending a half-finished garment, such as the bra, to an electronic component manufacturer for installing the electronic components and sending the half-finished garment with the installed electronic components back to the garment manufacturer for the finishing stage. Moreover the recycling of the garments after their lifetime is very easy, thanks for the current invention, namely the electronics is very easy and fast to remove e.g. just cutting the left side wing away, and in particularly in the embodiment where the garment or bar does have the electronic components in the module. In addition the manufacturing of the seams is very easy, because all the measuring techniques and the electronics can be built in a one textile module or piece.

The exemplary embodiments presented in this text are not to be interpreted to pose limitations to the applicability of the appended claims. The verb "to comprise" is used in this text as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific example embodiments when read in connection with the accompanying drawings.

BRIEF DESCRIPTION OF THE DRAWINGS

Next the invention will be described in greater detail with reference to exemplary embodiments in accordance with the accompanying drawings, in which:

FIG. 3 illustrates an exemplary module wing structure for a bra for measuring a physiological signal according to an advantageous embodiment of the invention; and FIG. 4 illustrates another example of the bra for measuring a physiological signal with a module wing structure according to an advantageous embodiment of the invention.

DETAILED DESCRIPTION

Figure 1:
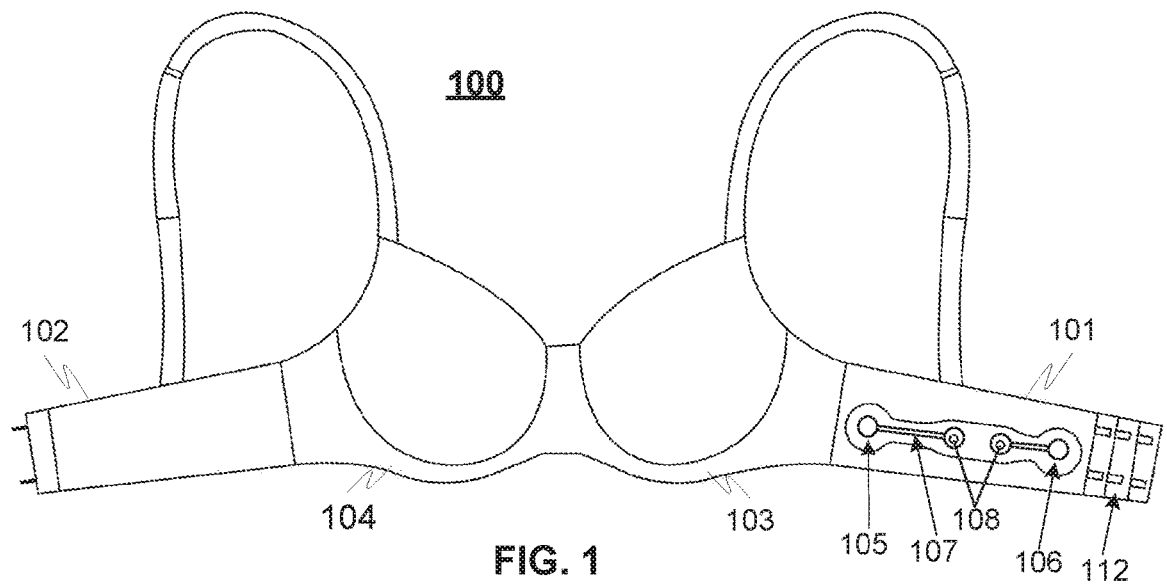
FIG. 1 illustrates a principle of an exemplary bra for measuring a physiological signal according to an advantageous embodiment of the invention.
Figure 2:
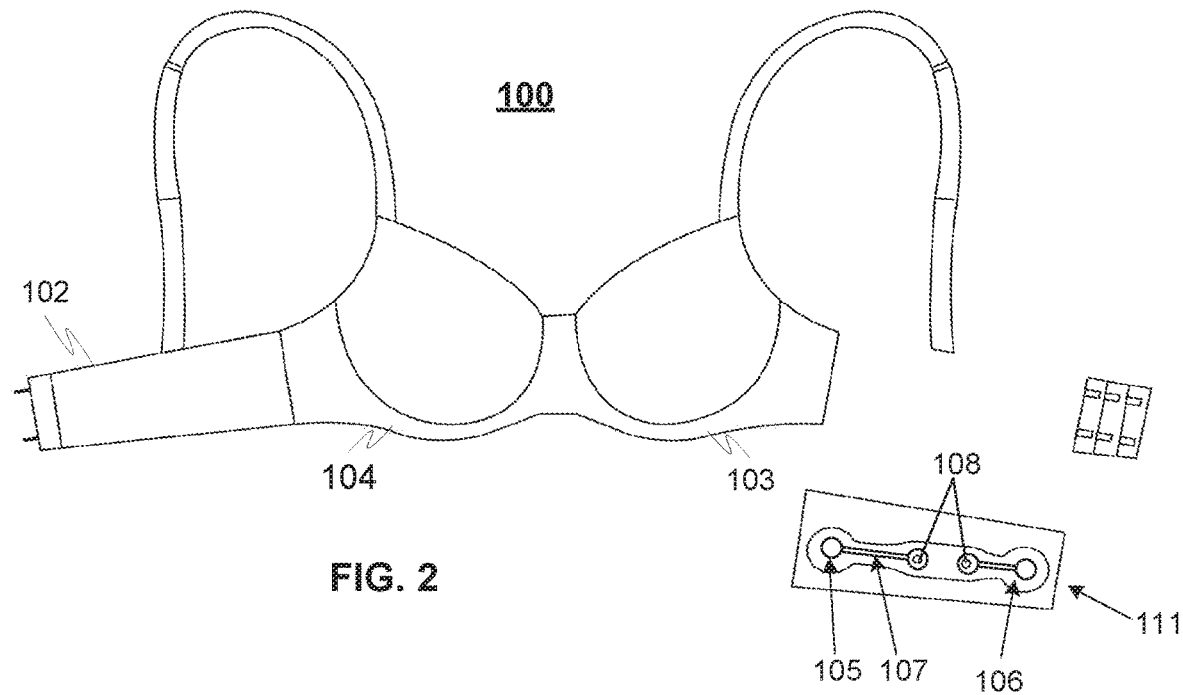
FIG. 2 illustrates an exemplary bra for measuring a physiological signal with a module wing structure according to an advantageous embodiment of the invention.

FIGS. 1 and 2 and 4 illustrate a principle of an exemplary bra 100 for measuring a physiological signal according to an advantageous embodiment of the invention, where the bra 100 comprises first (left) 103 and second (right) 104 front portions, where the bra cups locate. In addition the bra comprises also first (left) 101 and second (right) 102 side wings. As can be seen in the Figures the first end of the left side wing 101 is coupled with the first front portion 103 and the first end of the second side wing 102 with the second front portion 104. The second ends of the side wings 101, 102 are extended so that they can be connected to each other in the back side of the used during the use.

The measuring device and/or the electrodes 105, 106 is/are arranged to the first 101 side wing of the bra. The electrodes 105, 106 can be located such that a positive electrode 105 is integrated into the fabric just left to the left side cup 103. The negative electrode 106 is integrated into the fabric that extends over the left side of the body towards the back. The electrode location is next to the bra back hook-loop mechanism 112. This electrode setup measures nearly the same amplitude ECG as from the usual front electrode positions, and can be used to detect heart rate reliably. In order for the daily worn bra to be comfortable, the side fabrics joining the cups and encircling the body need to allow equal stretch. The conductive lead fabric can be attached to the fabric using non-continuous heat bonding membranes, which can be for example perforated material or having through holes or punctures through the material and/or attached only via spot-like locations (i.e. not attached uniformly and continuously in every points).

The bra comprises also conductive lead material 107 integrated to the first side wing 101 material. The bra comprises also connectors 108 and leads 107 for electrically coupling the electrodes 105, 106 and connectors 108. The connectors and leads are both arranged to the first side wing 101, as can be seen in FIGS. 1, 2 and 3. In addition the bra may also comprise a data measuring or processing unit 109, transmitter 109 and/or power source 110, which are also advantageously arranged to the first side wing 101.

FIGS. 2 and 3 illustrate an exemplary module wing structure 111 for a bra 100 for measuring a physiological signal according to an advantageous embodiment of the invention, where it can be seen that the measuring devices or electrodes 105, 106, connectors 108, leads 107 as well as measuring and processing unit 109, transmitter 109 and/or power source 110 can be arranged to the module 111. The module 111 can form said first side wing 101 as such or a portion of the first side wing 101, which can then be integrated to the bra 100 as the first side wing 101 as such or as a portion of the first side wing 101. The module 111 can be integrated e.g. by sewing or laminating, and it can comprise a suitable area, such as peripheral band or strip for integration process.

FIG. 4 illustrates very similar bra construction for measuring a physiological signal with a module wing structure according to an advantageous embodiment of the invention as is depicted in FIG. 2. In FIG. 4 it is still emphasized that the module forms the bearing structure or major portion of the first side wing of the bra, but still there might be a trim or stitching ribbon 113 or other minor portion added for example to support and fasten the module to the other structure of the bra.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims.

The features recited in dependent claims are mutually freely combinable unless otherwise explicitly stated. Especially it should be noted that the measuring device located in the left side wing may comprise electrodes and suitable leads and connectors, as well as other measuring components.

The invention claimed is:

1. A bra comprising:
   a first front portion having a medial end and a lateral end opposite the medial end;
   a second front portion having a medial end and a lateral end opposite the medial end, the medial end of the second front portion coupled to the medial end of the first front portion;
   a first side wing coupled with the lateral end of the first front portion,
      wherein the first side wing comprises a trim ribbon and a module wing structure,
      wherein the trim ribbon is coupled with the lateral end of the first front portion and configured to support and fasten the module wing structure to the lateral end of the first front portion, and
      wherein the module wing structure is integrated to the trim ribbon by sewing the module wing structure to the trim ribbon;
   a second side wing coupled with the lateral end of the second front portion; and
   a device for measurement of a physiological signal from a body of a user wearing said bra secured to the module wing structure, wherein:
      the device is integrated to the module wing structure;
      the device and the module wing structure together form a module wing assembly having a relatively flat surface configured to form a skin-tight fit when the bra is worn by the user,
         wherein the device comprises at least two electrodes secured to the first side wing,
         wherein the at least two electrodes are washable dry electrodes that do not require use of conductive gel; and
      the module wing assembly is located entirely on the first side wing.

2. The bra of claim 1, further comprising:
   connectors and leads, said leads being arranged to couple said at least two electrodes and said connectors electrically to each other,
   wherein said connectors and said leads are secured to said first side wing.

3. The bra of claim 2, wherein said connectors and said leads are secured to the module wing structure and wherein said module wing structure is integrated to said bra as said first side wing.

4. The bra of claim 1, wherein said at least two electrodes are secured to said module wing structure and wherein said module wing structure is integrated to said bra as said first side wing.

5. The bra of claim 1, further comprising:
   a processing unit, a transmitter, and a power source secured to said first side wing.

6. The bra of claim 5, wherein said processing unit, said transmitter, and said power source are secured to the module wing structure, and wherein said module wing structure is integrated to said bra as said first side wing.

7. The bra of claim 1, wherein said bra is one of a daily worn bra or leisure bra.

8. The bra of claim 1, wherein the physiological signal from the body of the user is an electric signal, and wherein the electric signal is at least one of an electrocardiogram signal for heart rate detection, bioimpedance, or an electro dermal activity signal.

9. The bra of claim 1, wherein said device is at least one of optical, temperature, or strain gauge.

10. The bra of claim 1, wherein said module wing structure forms at least a major portion of the first side wing of the bra.

11. A method for manufacturing a bra comprising:
   providing a first front portion having a medial end and a lateral end opposite the medial end and a second front portion having a medial end and a lateral end opposite the medial end and a first side wing and a second side wing,
   coupling the first side wing with the lateral end of the first front portion and the second side wing with the lateral end of the second front portion;
   providing a device for measuring a physiological signal from a body of a user wearing said bra; and
   integrating said device to a module wing structure,
      wherein the first side wing comprises a trim ribbon and the module wing structure,
      wherein the trim ribbon is coupled with the lateral end of the first front portion and configured to support and fasten the module wing structure to the lateral end of the first front portion,
      wherein the module wing structure is integrated to the trim ribbon by sewing the module wings structure to the trim ribbon,
      wherein the device is integrated to the module wing structure,
      wherein the device comprises at least two electrodes secured to the first side wing,
      wherein the at least two electrodes are dry electrodes, and
      wherein the module wing structure is located entirely on the first side wing.

12. The method of claim 11,
   wherein said at least two electrodes comprise a positive electrode between a negative electrode and the first front portion of the bra.

13. The method of claim 12, further comprising:
providing connectors and leads; and
coupling said at least two electrodes and said connectors electrically by said leads so that said connectors and said leads are secured to said module wing structure, wherein said module wing structure forms said first side wing.

14. The method of claim 13, further comprising:
securing said connectors and said leads to said module wing structure; and
integrating said module wing structure to said bra as said first side wing.

15. The method of claim 14, further comprising:
securing a processing unit, a transmitter, and a power source to said module wing structure.

16. The method of claim 11, further comprising:
providing a processing unit, a transmitter, and a power source into said module wing structure, said module wing structure forming said first side wing.

17. The method of claim 11, wherein the device is at least two electrodes and the method further comprising:
integrating said module wing structure to said bra as said first side wing.

18. The method of claim 11, wherein said module wing structure forms the first side wing of the bra in its entirety.

\* \* \* \* \*